United States Patent [19]

Montplaisir et al.

[11] Patent Number: 5,545,525
[45] Date of Patent: Aug. 13, 1996

[54] DETECTION OF CANDIDA ALBICANS

[75] Inventors: Serge Montplaisir, Lanoraie; Stéphane Mercure, Laval; Guy Lemay, Outremont, all of Canada

[73] Assignee: Universite de Montreal, Montreal, Canada

[21] Appl. No.: 207,402

[22] Filed: Mar. 7, 1994

[51] Int. Cl.[6] .......................... C07H 21/02; C07H 21/04; C12P 15/34; C12Q 1/68
[52] U.S. Cl. .............. 435/6; 435/7.2; 435/91.1; 435/91.2; 536/24.3; 536/24.32; 536/24.33
[58] Field of Search .................. 435/6, 7.21, 91.1, 435/91.2; 536/24.3, 24.32, 24.33

[56] References Cited

U.S. PATENT DOCUMENTS 4,874,695 11/1989 Pincus ............................... 435/19

OTHER PUBLICATIONS

Sequence Search Printout (Nov. 10, 1994), pp. 1–10.
Niegters et al. J. Clin. Microb. 31(4) pp. 904–910, 1993.
Mason et al. J. Clin. Microb. 25 (3) pp. 563–566, 1987.
Mercure et al. Nuc. Acid. Res. 21(25) pp. 6020–6027, 1993.
Mercure et al. Nuc. Acid. Res. 21(6) p. 1490, 1993.
Edwards, J. E., "Invasive Candida infections:" N. Engl. J. Med., 1991, 324(15):1060–1062.
Scherer, S. et al., J. Clin. Microbiol., 1986, 25:675–679.
Scherer, S. et al., P.N.A.S. USA, 1988, 85:1452–1456.
Maniatis, T. et al., Molecular Cloning, A Laboratory Manual, Second Ed., Cold Spring Harbor University Press, Cold Spring Harbor. 1989 Whelan et al., Antimicrob. Agents Chemother., 1986, 29:726–729.
Cech, T. R., Gene, 1988, 73:259–271.
Schmid et al., J. Clin. Microbiol., 1990, 28:1236–1243.

Primary Examiner—W. Gary Jones
Assistant Examiner—Paul B. Tran
Attorney, Agent, or Firm—Klauber & Jackson

[57] ABSTRACT

The present invention relates to a DNA probe adapted to be used as a PCR target for the detection of the presence of *C. stellatoidea* and a subgroup of *C. albicans* strains in a biological sample, which comprises the nucleic acid sequence set forth in SEQ ID NO:1 or any functional analogs thereof wherein the hybridization of the probe and the rRNA of *C. albicans* is substantially preserved. The present invention also relates to a method for the detection of trace amount of *C. stellatoidea* or a subgroup of *C. albicans* in a biological sample, which comprises the steps of: a) isolating DNA from said biological sample; b) amplifying said isolated DNA of step a) with paired oligonucleotides: 5' primer: 5' AAC TTA GAA CTG GTA CGG 3' (SEQ ID NO:2), 3' primer: 5' AGT AGA TAG GGA CAG TGG 3' (SEQ ID No:3); or 5' GAC TCT CAA CCT ATA AGG 3' (SEQ ID NO:4), 3' primer: 5' TTA AGC ATT GCT CCA AGA 3' (SEQ ID NO:5); c) isolating amplified DNA of step b) and determining the presence or absence of *C. stellatoidea* or a subgroup of *C. albicans* in said biological sample by direct examination of the amplified products on stained gel or by hybridization of the amplified product with the DNA segment used as target.

3 Claims, 1 Drawing Sheet

DETECTION OF CANDIDA ALBICANS

BACKGROUND OF THE INVENTION (a) Field of the Invention

The invention relates to genomic probes for the detection of the presence of *Candida albicans* in a biological sample.

(b) Description of Prior Art

Systemic infection by fungi is an increasing problem, especially in immunocompromised and leukemic patients. Candida species are the most common of these fungal pathogen representing approximately 8% of all microorganisms recovered from blood (*C. albicans* account for more than 60% of these isolates). Mortality rate in these individuals with candidemia has been reported to vary between 38 to 90% depending on the underlying therapeutic procedures and immune status of the patient. A disturbingly large number of these patients die with undiagnosed invasive Candida infections.

The diagnosis of systemic candidiasis has been problematic even though patients may have extensive invasive Candida infections of several deep organs. In fact, it is evaluated that only 30 to 50% of all patients with disseminated *C. albicans* infections are blood culture positive (Edwards, J. E., *Invasive Candida infections N. Med.*, 1991, 324(15):1060–1062).

Current techniques for the detection and identification of fungi mainly involve culture. This long-available method often proves too slow, cumbersome and insensitive ($>10^3$ yeast per ml) in clinical settings. Detection of a variety of antibodies and antigens in invasive candidiasis has also been extensively investigated, but with limited success. Thus, there is crucial need for a fast, accurate and effective test to diagnose deep-seated Candida infections.

U.S. Pat. No. 4,874,695, which issued on Oct. 17, 1989 to Pincus, discloses a method for identification of fungal microorganisms, characterized as "rapid". It involves culturing the microorganisms for 2 to 3 days, preparing an inoculum from the culture, mixing the inoculum with a chromogenic substrate (or separately with more than one such substrate) for detecting the presence or absence of one or more of acetate esterase, leucylglycine aminopeptidase and glycylglycine aminopeptidase by formation of a colored product or a product convertible to a colored product, and incubating the inoculum/substrate mixture(s) for 2 to 6 hours, whereby the unknown microorganism is identified by comparing with the enzyme activity of known genera and species. Thus, the overall procedure takes 2 to 3 days plus 2 to 6 hours. However, the sensitivity of this method is restricted by culture.

Other known methods are the so-called gold standard diagnosis which employs culturing in different media; and a method using monoclonal antibodies combined with latex agglutination. In a well-established method, potassium hydroxide solution is applied to a smear sample on a glass slide, whereby all cells are destroyed except *Candida* hyphae and spores, a microscopic examination being carried out to identify the organism. This (KOH) method is, however, subjective and requires considerable laboratory skills.

An initial step in DNA-based methods for typing Candida species and strains, is direct examination of the fluorescence pattern obtained after restriction digests of total genomic DNA and electrophoresis. These DNA fingerprints distinguish Candida species and many *C. albicans* subtypes (Scherer, S. et al., *J. Clin. Microbiol.*, 1986, 2.5:675–679).

One drawback of this approach is that only a limited number of sites in the genome of a given species can be scored for differences, primarily the highly conserved ribosomal DNA and the mitochondrial DNA.

Species-specific DNA probes that recognizes repetitive sequences of the *Candida albicans* genome were also described by Scherer et al. (*P.N.A.S. USA*, 1988, 85:1452–1456) and Soll et al. (*J. Clin. Microbiol.*, 1990, 28:1236–1243). These DNA segments present the advantage of being species-specific, hybridizing with *C. albicans* as well as *C. stellatoidea*. However numerous drawbacks can be identified: the nature of these fragments remain unknown and, the patterns obtained are complex and only relatively constant in time. Moreover, these segments cannot be used as PCR targets since their complete sequences remain unknown.

Since Polymerase Chain Reaction (PCR) analysis of clinical samples is gradually becoming incorporated into diagnostic laboratory practice, this method could provide an interesting alternative to present diagnostic methods for fungi. In fact, PCR amplification of specific regions in the genome of a variety of lower eukaryotes has been shown to allow rapid identification of these microorganisms.

Recently, the polymerase chain reaction was used to detect, in clinical specimens, a DNA sequence coding for cytochrome $P_{450}L_1A_1$, a single copy fungus-specific gene. This Polymerase Chain Reaction (PCR) method was able to detect the presence of as few as 100 organisms per ml in a variety of clinical specimens. However, this method is not specific to any particular fungi.

Genes coding for ribosomal RNA are attractive targets for PCR based detection schemes as sensitivity is likely to be higher than in schemes designed to detect single copy genes since rDNA genes are present in multiple copies in each organism. Accordingly, a PCR method based on the detection of a segment of the 18S rRNA gene was shown to detect as few as 15 cells per ml. This target sequence was however conserved throughout the fungal kingdom.

There is still no reliable single step technique available for routine detection and species identification of the most common pathogenic genus in fungi, Candida sp. Thus, it would be highly desirable to obtain a PCR test for the inter-species discrimination of fungi.

*C. albicans* is a primary concern since it represents the most common fungal human pathogen in vaginal, systemic and nosocomial infections. However, identification of Candida species remains important since the incidence of non-*C. albicans* infections is rising, and these yeasts are not eradicated as effectively with current drug therapies.

Thus, it would be highly desirable to be provided with means to detect trace amount of *Candida albicans* present in a biological sample and with a suitable gene for the detection, identification and speciation of Candida sp.

SUMMARY OF THE INVENTION

One aim of the present invention is to provide for means to detect trace amount of *Candida albicans* in a biological sample.

In accordance with the present invention, a suitable gene for the detection, identification and speciation of Candida sp. is the 25S rRNA gene, which general displays more variation than the 18S rRNA gene.

The sequence of a small DNA fragment specific to *C. stellatoidea* and a subgroup of *C. albicans* (several authors are presently suggesting that *C. stellatoidea* should be included in the *C. albicans* species as a sucrose-negative mutant) which presence correlates with the sensitivity to an antifungal agent 5-fluorocytosine, also known as flucytosine, was isolated. Consequently, this fragment, which has been identified as a group I intron, is used in accordance with the present invention as a PCR target or as a probe for detection of the specific amplified products. In view of its correlation with susceptibility to an antifungal agent, its detection could also assist in selecting optimal chemotherapeutic regimens. Moreover, this fragment may also be useful as a model to study new antifungal agents since the presence of group I self-splicing introns in the rRNA genes of *P. carinii*, *C. stellatoidea*, and *C. albicans* subgoup distinguishes these organisms from their mammalian host. Since various compounds can specifically inhibit the splicing of group I introns in vitro, group I intron splicing from transcripts of nuclear genes provides a specific target for development of new therapeutic agents against these fungal pathogens. Since no long-term culture method exist for *P. carinii*, *C. albicans* can be simultaneously used as a model to study this hypothesis.

Since the probe of the present invention is specific to a subgoup of *C. albicans*, and a close relative *C. stellatoidea*, it can be used as an identification tool in clinical microbiology laboratories as part of a kit. Detection of this DNA fragment eliminates all the problems and disadvantages encountered with methods in current use (culture, antibodies and antigen detection. It greatly reduces the time presently required to identify *C. albicans* in clinical laboratory, since it can be used directly on clinical specimens with only a short pre-treatment of the specimen to allow the release of fungal DNA.

In accordance with the present invention, the presence or absence of this new group I intron, located in the 25S nuclear rRNA-encoding gene, accounts for the difference observed in the rDNA of *C. albicans* (3.7/4.2 kbp fragments).

In accordance with the present invention, a correlation between the presence of a single dimorphic restriction fragment, generated by EcoRI digestion of total DNA, and susceptibility to the antifungal agent 5-FC, and its derivative 5-FU, has been established.

In accordance with the present invention there is provided a DNA probe adapted to be used as a PCR target for the detection of the presence of *C. stellatoidea* and a subgroup of *C. albicans* strains in a biological sample, which comprises the following nucleic acid sequence:

```
CAACCTATAA  GGGAGGCAAA  AGTAGGGACG

CCATGGTTTC  CAGAAATGGG   50

CCGCGGTGTT  TTTGACCTGC  TAGTCGATCT

GGCCAGACGT  ATCTGTGGGT  100

GGCCAGCGGC  GACATAACCT  GGTACGGGGA

AGGCCTCGAA  GCAGTGTTCA  150

CCTTGGGAGT  GCGCAAGCAC  AAAGAGGTGA

GTGGTGTATG  GGGTTAATCC  200

CGTGGCGAGC  CGTCAGGGCG  CGAGTTCTGG

CAGTGGCCGT  CGTAGAGCAC  250

GGAAAGGTAT  GGGCTGGCTC  TCTGAGTCGG

CTTAAGGTAC  GTGCCGTCCC  300

ACACGATGAA  AAGTGTGCGG  TGCAGAATAG

TTCCCACAGA  ACGAAGCTGC  350

GCCGGAGAAA  GCGATTTCTT  GGAGCAATG

379
```

SEQ ID NO: 1 or any functional analogs thereof wherein the hybridization of the probe and the rRNA of *C. albicans* is substantially preserved.

In accordance with the present invention, there is also provided a method for detection of trace amount of *C. stellatoidea* or a subgroup of *C. albicans* in a biological sample, which comprises the steps of:

a) isolating DNA of from said biological sample;

b) amplifying said isolated DNA of step a) with paired oligonucleotides:

```
5'primer: AAC  TTA  GAA  CTG  GTA  CGG  3'  (SEQ ID NO: 2)

3'primer: AGT  AGA  TAG  GGA  CAG  TGG  3'  (SEQ ID NO: 3)

or
5'primer: GAC  TCT  CAA  CCT  ATA  AGG  3'  (SEQ ID NO: 4)

3'primer: TTA  AGC  ATT  GCT  CCA  AGA  ;  (SEQ ID NO: 5)
``` c) isolating amplified DNA of step b) and determining the presence or absence of *C. stellatoidea* or a subgroup of *C. albicans* in said biological sample by direct examination of the amplified products on stained gel or by hybridization of the amplified product with the DNA segment used as target.

DETAILED DESCRIPTION OF THE INVENTION

Figures 1A, 1B:
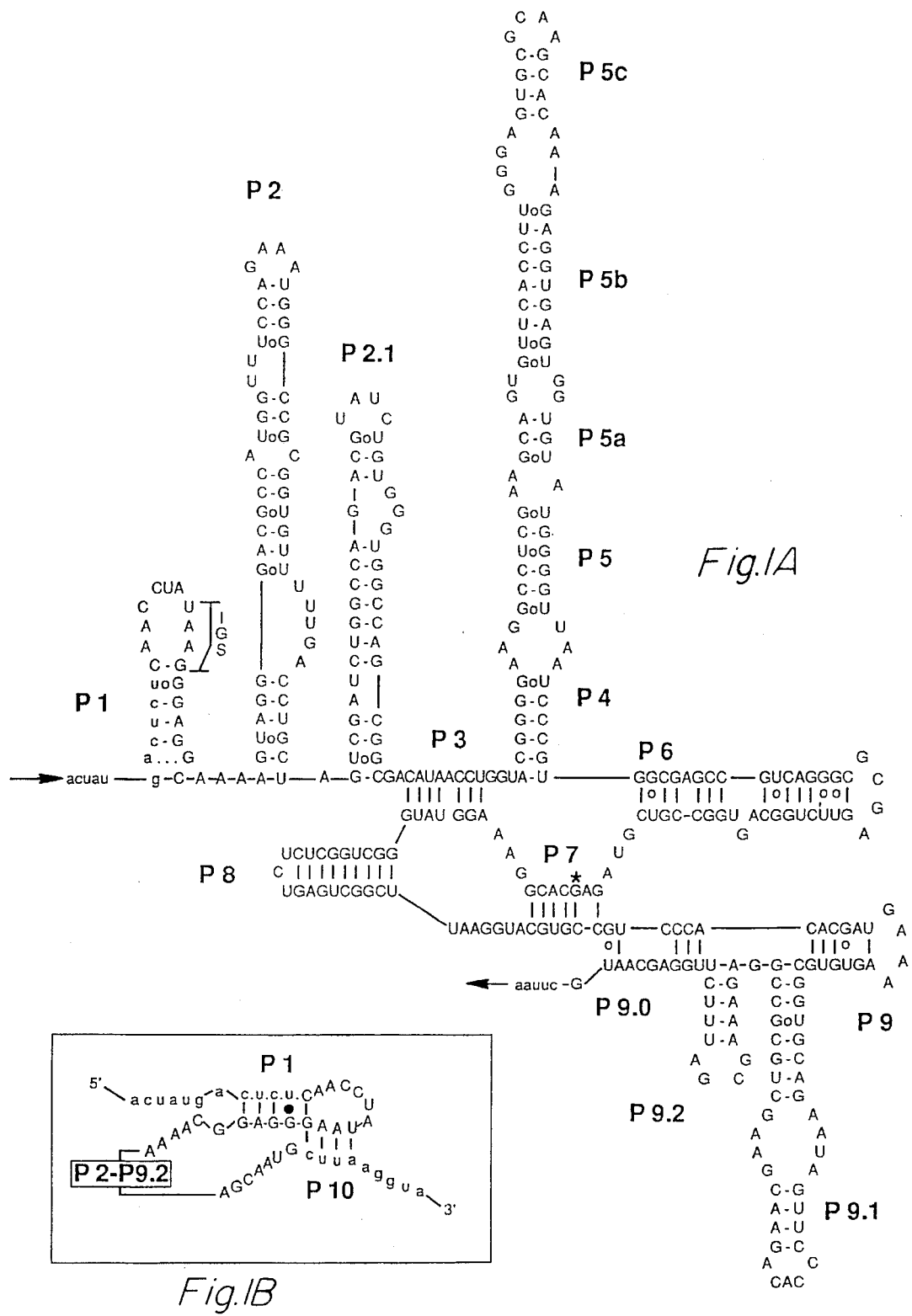
FIG. 1 illustrates the predicted secondary structure of *C. albicans* group I intron (A) Potential secondary structure of the intron. (B) Inset showing detail of potential secondary structure of P1 loop with 3' end of the intron (IGS in FIG. 1A).

The DNA probe of the present invention provides the basis for the development of a PCR and hybridization assay. Detection of trace amount of *C. stellatoidea* and *C. albicans* subgroup in usually sterile biological samples, such as blood and cerebrospinal fluids, would be possible. However, a quantitative PCR evaluation would be required to correlate a positive result to clinical significance in other anatomical sites such as skin, gastrointestinal tract, and vagina, since *C. albicans* is a member of the natural flora in these sites.

A small fragment of chromosomal DNA only observed in a subgroup of *C. albicans* strains has been isolated from a clinical strain. This 379 base pairs (bp) fragment is located at nucleotide 2245 of the 25S rRNA gene and has been identified as a group I intron. Its presence was shown to correlate with susceptibility to an antifungal agent, 5-fluorocytosine.

Demonstration of the correlation with susceptibility

Twelve collection strains, obtained either from the American Type Culture Collection or from the Institut Pasteur, and 108 independently isolated clinical strains identified as *C. albicans* were examined by EcoRI Restriction Fragment Length Polymorphism (RFLP).

*C. albicans* DNA was prepared as follows. The strains were inoculated in 100 ml of Sabouraud™ dextrose broth and incubated under agitation at 37° C. overnight. Cells were harvested and incubated for 30 min. at 22° C. in 10 ml of sorbitol buffer (1.2M sorbitol, 50 mM citrate/50 mM phosphate [pH 5.6]) containing 1% β-mercaptoethanol. Cells were centrifuged and resuspended in 2.5 ml of 1.2M sorbitol, 50 mM citrate/50 mM phosphate (pH 5.6), 50 mM EDTA, 0.1% β-mercaptoethanol, containing 01 µg of Zymolyase 20T (ICN Immunobiologicals, Lisle, IL) per ml for 45 min. at 30° C. The resulting spheroplasts were collected and resuspended in 12 ml of 50 mM Tris-HCl (pH 7.5), 20 mM EDTA, 1% SDS. After 30 min. at 65° C., 3 ml of 3M potassium acetate was added, and the suspension was placed on ice for 60 min. After centrifugation, two volumes of ethanol were added to the supernatant. The precipitated nucleic acids were dissolved in 3 ml of 10 mM Tris-HCl (pH 7.5), 1 mM $Na_2EDTA$ (TE buffer) containing 10 µg of ribonuclease A (Sigma) and 10 µg of proteinase K (Sigma) per ml. After a 3 hr incubation at 50° C., the DNA was further purified by phenol:chloroform extraction and precipitated with one volume of isopropanol. The resulting DNA was dried, dissolved in TE buffer and 5 µg of total genomic DNA was digested overnight at 37° C. with 10 units of EcoRI enzyme in 2× One-Phor All Buffer™ (Pharmacia). To ensure complete digestion, a further 10 units of EcoRI was added after 18 hr, and incubation was continued for 5 hr at 37° C. Then, a dye mix containing 10% glycerol and 0.1% bromophenol blue was added to each sample before separation of the resulting fragments on 25 cm, 0.8% agarose gels. The migration was carried out at 50 V for 20 hr in Tris-acetate-EDTA buffer (Maniatis, T. et al., *Molecular Cloning, A Laboratory Manual*, Second Edition. Cold Spring Harbor University Press, Cold Spring Harbor., 1989). Gels were stained for 30 min. with 1 µg/ml of ethidium bromide. HindIII digested lambda DNA and 1 kb DNA Ladder™ (BRL) were used as size markers. Strains analyzed in this way were assigned to either of two major DNA type subgroups. This delineation was realized, on the basis of a major dimorphic fragment, which present, for a given *C. albicans* strain a size of 3.7 kbp (DNA type IA) or 4.2 kbp (DNA type IB). 62.5% (75/120) of strains were of DNA type IA and 37.5% of DNA type IB.

The susceptibility to 5-FC (Sigma) and 5-FU (Sigma) of the 120 *C. albicans* strains was determined on Yeast Nitrogen Base agar (Difco) as previously described (Whelan et al., *Antimicrob. Agents Chemother.*, 1986, 29:726–729). Collection strains with known 5-FC susceptibility (American Type Culture Collection, 12301 Parklawn Drive, Rockville, Md 20852 USA; ATCC accession number 44373: resistant; ATCC accession number 44374: sensitive) were included in each experiments. Strains were considered resistant when they had Minimal Inhibitory Concentration values equal or greater than 25 µg/ml to 5-FC (incubation of 48 hours at 37° C.) and greater than 100 µg/ml to 5-FU (incubation of 5 days at 37° C.).

Group-specific differences were identified when DNA type subgroups and 5-FC susceptibility were compared for each of the 120 *C. albicans* strains. As shown in Table 1 below, DNA type IA (3.7 kbp) strains appeared heterogeneous, but were mostly resistant to 5-FC ($p<0.001$). DNA type IB, on the other hand, consisted almost exclusively of sensitive strains ($p<0.001$). Further comparison between DNA type and 5-FU susceptibility, an active metabolic by-product of 5-FC, revealed similar significant correlation. Results for 5-FU susceptibility were identical to those obtained with 5-FC for all DNA type IA and the majority of DNA type IB strains. Only the four 5-FC resistant strains of DNA type IB presented a change of susceptibility between 5-FC and 5-FU, creating a perfect correlation between the presence of the 4.2 kbp fragment and strain susceptibility to 5-FU.

TABLE 1

Correlation between dimorphic type of *C. albicans* and susceptibility to 5-FC and 5-FU

| | EcoRI RFLP DNA Type | |
|---|---|---|
| Susceptibility to | IA (3.7 kbp) n = 75 | IB (4.2 Kbp) n = 45 |
| 5-fluorocytosine | | |
| Sensitive | 29 (38.7%) | 41 (91.1%) |
| Resistant | 46 (61.3%) | 4 (8.9%) |
| 5-fluorouracil | | |
| Sensitive | 29 (38.7%) | 45 (100%) |
| Resistant | 46 (61.3%) | 0 |

The isolation of the fragment

Hybridization of DNA complementary to rRNA from *C. albicans* confirmed that the 3.7 and 4.2 kbp EcoRI fragments were actually sequences encoding rRNA. Furthermore, specific cross-hybridization of the gel-purified 3.7 and 4.2 kbp fragments to their counterpart in whole cell DNA digests suggests that they encode homologous sequences- To understand the observed correlation and the nature of this dimorphism, a complete basic rDNA repeat unit of a type IB strain was cloned (4-1, isolated from the vagina of a patient with well-documented recurrent vulvovaginal candidiasis).

Genomic DNA was digested with BglII (Pharmacia). Resulting fragments were loaded on a 1% low melting point agarose gel. The intensely staining band corresponding to the basic rDNA repeat unit was purified by Elutip-d™ (Schleicher & Schuell Inc., Keene, N.H.), ligated to Lambda EMBL3 BamHI arms (Promega), and packaged in-vitro (BRL). The partial library obtained was screened for complete basic ribosomal repeat unit by standard plaque hybridization procedure (Maniatis, T. et al., *idem*) using gel-purified 3.7 kbp fragment (type IA) as a probe. Positive clones were double-digested with EcoRI and SalI and subcloned in Bluescript plasmid. Subclones still hybridizing with the 3.7 kbp fragment were then subjected to the exonuclease III deletion procedure (Stratagene) and sequenced on both strands by the dideoxymethod using Sequenase DNA polymerase (US Biochemicals). Confirmation of ambiguous nucleotides was achieved by priming the sequencing reaction with internal oligonucleotides. An insertion of 379 base pairs inserted in a conserved region of eukaryotic rRNA, immediately after nucleotide 2245 of *C. albicans* 25S rRNA, was found.

In accordance with the present invention, a new group I intron was isolated. This fragment was identified as such by the following demonstrations.

1. Its absence from mature rRNA as confirmed by Northern hybridization

To determine if the *C. albicans* insertion is present in mature rRNA, primers were designed to amplify this additional sequence element in order to use it as a probe. Two 24-mer oligonucleotide primers were derived from the sequence of the intron and adjacent regions, and modified to include an EcoRI site. The clockwise primer (SEQ ID NO:6) (5'-TAT GAC TCT GAA TTC CTA TAA GGG-3') begins 9 nucleotides upstream of the intron insertion site while the second primer (SEQ ID NO:7) (5'-CTA CCT TAA GAA TTC CTC CAA GAA-3') begins 10 nucleotides downstream of the intron 3' end in counterclockwise direction (SEQ ID NO:1). They were then used for the PCR amplification of the intron from a cloned rDNA subfragment of strain 4-1 (SUBFRAGMENT I). Reaction mixes were prepared according to GeneAmp\AmpliTaq™ PCR kit instructions (Perkin-Elmer). Thirty cycles of amplification were performed in a DNA Thermal Cycler™ (Perkin-Elmer) by incubations at 94° C. for 1 min., 50° C. for 2 min. and 72° C. for 2 min. No signal could be detected upon hybridization of the amplified insertion to a Northern transfer of total *C. abicans* RNA from stationary phase cultures of four strains of each DNA type. 2. Its putative secondary structure folding.

This *C. albicans* intron displays a potential secondary structure comparable to all known group I introns (Cech, T. R., *Gene*, 1988, 73:259–271). This intron exhibits the somewhat conserved elements that allow formation of the characteristic catalytic core structure which invariably includes six nucleotides: presence of a U immediately upstream of the 5' splice site; this U is base-paired with a G in the PI helix, a 3' terminal G residue, an A residue in J6/J7 (joining regions) preceding the P7 pairing and a centrally positioned G-C pairing in P7 (FIG. 1).

3. Its in vitro splicing capacity.

A Bluescript clone from strain 4-1, obtained after partial exonuclease deletion of subfragment I, was selected for its potential to generate distinct self-splicing products. One microgram of the plasmid was linearized with NarI and in vitro transcription using T7 RNA polymerase was allowed to take place for 1 hr at 37° C. in 80 mM Hepes-KOH pH 7.5, 16 mM $MgCl_2$, 2 mM spermidine, 10 mM DTT, 0.4 mM of each of the 4 nucleotides and 50 µCi of [alpha-$^{32}$P]UTP (800 Ci/mmol, New England Nuclear). The transcript products were extracted with phenol:chloroform, precipitated with ethanol, and purified on a 4% polyacrylamide-urea gel. The primary transcript was located by autoradiography, eluted overnight in distilled water at 4° C., and precipitated twice with ethanol. In vitro splicing reactions were performed with 5000 cpm of purified primary transcript in 50 mM Tris-HCl pH 8.0, 100 mM NaCl in the presence or absence of 0.2 mM GTP and 10 mM $MgCl_2$. Individual reactions were submitted to various time and temperature conditions. Fragments generated were analyzed on a 6% polyacrylamide-urea gel.

The autocatalytic process of self-splicing was observed only in the presence of GTP and $MgCl_2$ at 37° C. and 56° C. A 379 bases product, corresponding to the intron, and a 318 bases fragment corresponding to the ligated exons were both generated confirming the self-splicing capacity of this sequence element.

To analyze the distribution of this group I intron in the Candida genus, the following oligonucleotides were designed:

The oligonucleotides from pair A are derived from highly conserved regions of the rDNA sequence flanking the intron and are thus non-specific to Candida species:

5'primer: AAC TTA GAA CTG GTA CGG 3' (SEQ ID NO: 2)

3'primer: AGT AGA TAG GGA CAG TGG 3' (SEQ ID NO: 3)

The oligonucleotides from pair B are derived from the intron sequence and are slightly overlapping the flanking rDNA sequences (these primers are specific to the described group I intron):

5'primer: GAC TCT CAA CCT ATA AGG 3' (SEQ ID NO: 4)

3'primer: TTA AGC ATT GCT CCA AGA 3' (SEQ ID NO: 5)

With these two sets of primers, the distribution of this group I intron was studied. Several representative of the following species were analyzed: *C. glabrata, C. kefyr, C. pseudotropicalis, C. utilis, C. tropicalis, C. krusei, C. guillermondii, C. rugosa, C. parapsilosis, C. norvegensis and C. zeylanoides*. We also included in this study, non pathogenic yeast strains like *Saccharomyces cerevisiae, Kluyveromyces lactis, Torulopsis candida, C. antartica, C. humicola, C. haemulonii, C. japonica, C. lipolytica, C. paratropicalis, C. viswanathii*.

DNA extraction was performed as described above. PCR reaction mixtures were prepared according to GeneAmp\AmpliTaq™ PCR kit instructions (Perkin-Elmer). Forty cycles of amplification were performed in a DNA Thermal Cycler™ (Perkin-Elmer) by incubations at 94° C. for 1 min., 50° C. for 2 min. and 72° C. for 2 min. Resulting amplified products were analyzed on 0.8% agarose gels stained with ethidium bromide. As expected, the first set of primers was not specific to Candida species Therefore, a fragment was generated for all strains tested. However this fragment appeared larger in size for *C. stellatoidea* and the 4.2 kbp subgroup of *C. albicans* indicating the presence of an additional sequence element. The second pair of primers (B) confirmed that this additional sequence element is indeed the intron since amplified products were only observed for strains from *C. stellatoidea* and the 4.2 kbp subgroup of *C. albicans*. These primers are thus specific to the intron sequence. Group I introns being poorly conserved in primary sequence, these primers remain specific to the Candida intron.

To complete the specificity tests of this sequence element two hybridization assay were performed. DNA extraction was performed as previously described. 5 µg of DNA from the various Candida strains was digested with EcoRI. The resulting fragments were migrated on a 0.8% agarose gel and transferred to a nylon membrane before hybridization with the sequence element. The intron sequence was cloned in Bluescript using the amplified product generated by the primers used in the Northern blot analysis which are modified to include an EcoRI site. The resulting plasmid was isolated by an alkaline lysis procedure (Maniatis, T. et al., *idem*) and the sequence element (Ca intron) was purified from low-melting point agarose gel by Elutip-d™ (Schleicher & Schuell Inc., Keene, N.H.). Probe was labeled with alpha $^{32}$P-dATP using a nick translation kit (BRL) according to the manufacturers' instructions and passed through a Sephadex™ G-50 (Pharmacia) column before use. Prehybridization was done for 3 hr at 65° C. in Hybaid Hybridization Oven™ (InterSciences Inc., Markham, Canada) in a solution containing 6× SSPE (Maniatis, T. et al., *idem*), 10× Denhardt's (Maniatis, T. et al., *idem*), 0.1% Triton™ X100, 1% Sarkosyl™ and 10 µg of t-RNA per ml. The filters (200 $cm^2$) were then hybridized overnight at 65° C. in 10 ml of the prehybridization solution containing 5% dextran sulfate and 1×10$^6$ cpm of radioactive DNA probe. The membranes were then washed twice for 20 min. at 65° C. in 2× SSPE, 0.1% Sarkosyl™ followed by two changes of 0.5× SSPE, 0.1% sodium pyrophosphate at 65° C. for 20 min. and one change of 0.1× SSPE, 0.1% sodium pyrophosphate. The wet blots were sealed in plastic bags and exposed at −70° C. with two Cronex Lightning-Plus™ intensifying screens (DuPont Co., Wilmington, Del.) and X-OMAT AR™ films (Eastman Kodak Co., Rochester, N.Y.). The 379 bp probe hybridized only to C. albicans strains from the 4.2 kbp subgroup and to C. stellatoidea strains. Moreover, the signal was specific, in both cases, to a fragment originating from the rDNA unit indicating that this sequence element is not dispersed in the genome.

The hybridization assay was also realized using the C. albicans intron labelled with T4 polynucleotide kinase and gamma $^{32}$P-dATP, which has the advantage of generating a full length probe. The results obtained confirmed those of the previous procedure.

In accordance with the present invention, the presence or absence of this new group I intron, located in the 25S nuclear rRNA-encoding gene, account for the difference observed in the rDNA 3.7/4.2 kbp fragments.

In accordance with the present invention, a correlation between the presence of a single dimorphic restriction fragment generated by EcoRI digestion of total DNA and susceptibility to the antifungal agent 5-FC, and its derivative 5-FU, has been established.

The cloned intron sequence of C. albicans may be used as a model to study potential inhibitor of self-spicing capable to act as antifungal agents. Such model may be applied to Pneumocystis carinii which possess a group I intron at the same ribosomal DNA location, but this microorganism cannot be studied directly as easily as C. albicans since it remains impossible to cultivate in vitro.

Such a model may also enable researchers to study and identify putative proteins involved in the self-spicing mechanisms of group I introns. Such proteins could also be consider as potential target for antimicrobial agents. These agents would be active against C. albicans, C. stellatoidea and P. carinii or any other microorganism presenting a group I intron which must be spliced for survival of the microorganism, such as ribosomal RNA introns.

Transfer of this intron sequence to Saccharomyces cerevisiae would be used as such an in vivo model.

The present invention will be more readily understood by referring to the following example which is given to illustrate the invention rather than to limit its scope.

EXAMPLE I

Detection of trace amounts of C. albicans

First, a method for rapid and efficient DNA extraction from C. albicans has been developed.

A culture of 10 ml in Yeast Nitrogen Base without amino acids is prepared overnight. The sample is centrifuged to harvest the yeast at 225 RPM at 30° C. These yeast cells are harvested in microtubes containing 1.5 ml of the culture. These harvested cells are resuspended in 500 µl of a 0.25M Tris/HCl buffer, pH 8.0, 1.5% sodium dodecyl sulfate (SDS). The microtubes containing yeasts are placed in a boiling water bath for a period of 30 minutes. The microtubes are then vortexed for 2 minutes before an extraction is performed using phenol:chloro-form:isoamylalcohol at a 25:24:1 ratio. The supernatant is recovered and precipitated with 2 volumes of 100% ethanol supplemented with 0.3M sodium acetate, pH 5.2. Precipitation is carried out for 30 min. on ice. This is followed by a centrifugation. The centrifuged tubes are rinsed with 70% ethanol and centrifuged again. The pellet is dried and resuspended in 50 µL of water. The concentration of the resulting DNA is then evaluated. Recovery yield should be between 10 and 20 µg with a purity satisfactory for PCR reactions.

The sensitivity of the PCR method combined to the DNA extraction protocol has been evaluated to approximately 10 cells per ml.

The following oligonucleotides from pair A have been used to test the sensitivity of the detection of the method in accordance with the present invention:

5'primer: AAC TTA GAA CTG GTA CGG 3' (SEQ ID NO: 2)

3'primer: AGT AGA TAG GGA CAG TGG 3' (SEQ ID NO: 3)

A yeast culture was diluted in water to obtain $10^1$, $10^2$, $10^3$ and $10^4$ cells/µl. Each of these solutions were subjected to the rapid DNA extraction method followed by the PCR reaction. Thus, the minimum quantity of yeast that must be present in the solution during the DNA extraction to ensure a direct visualization on gel of the amplified products (fluorescence detection) was of 100 yeast. If however, a DNA extract is diluted in water prior to PCR detection (1pg, 10pg, 100pg, 1 µg), there is obtained with the same oligonucleotides from pair A, a detection of 1pg of DNA, which correspond to about 25 yeasts.

The same experiment was conducted with the oligonucleotides from pair B, and the same results were obtained.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

---

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 379 base pairs
        ( B ) TYPE: nucleic acid (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

| | | | | | | |
|---|---|---|---|---|---|---|
| CAACCTATAA | GGGAGGCAAA | AGTAGGGACG | CCATGGTTTC | CAGAAATGGG | CCGCGGTGTT | 60 |
| TTTGACCTGC | TAGTCGATCT | GGCCAGACGT | ATCTGTGGGT | GGCCAGCGGC | GACATAACCT | 120 |
| GGTACGGGGA | AGGCCTCGAA | GCAGTGTTCA | CCTTGGGAGT | GCGCAAGCAC | AAAGAGGTGA | 180 |
| GTGGTGTATG | GGGTTAATCC | CGTGGCGAGC | CGTCAGGGCG | CGAGTTCTGG | CAGTGGCCGT | 240 |
| CGTAGAGCAC | GGAAAGGTAT | GGGCTGGCTC | TCTGAGTCGG | CTTAAGGTAC | GTGCCGTCCC | 300 |
| ACAGCATGAA | AAGTGTGCGG | TGCAGAATAG | TTCCCACAGA | ACGAAGCTGC | GCCGGAGAAA | 360 |
| GCGATTTCTT | GGAGCAATG | | | | | 379 |

(2) INFORMATION FOR SEQ ID NO:2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: 5 END PRIMER (iii) HYPOTHETICAL: NO (iv) ANTI-SENSE: NO (xi) SEQUENCE DESCRIPTION: SEQ ID NO:2:

AACTTAGAAC TGGTACGG                                                         18

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: 3 END PRIMER (iii) HYPOTHETICAL: NO (iv) ANTI-SENSE: NO (xi) SEQUENCE DESCRIPTION: SEQ ID NO:3:

AGTAGATAGG GACAGTGG                                                         18

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)
        (A) DESCRIPTION: 5 END PRIMER (iii) HYPOTHETICAL: NO (iv) ANTI-SENSE: NO ( x i ) SEQUENCE DESCRIPTION: SEQ ID NO:4:

GACTCTCAAC CTATAAGG                                                                                    18

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)
        ( A ) DESCRIPTION: 3 END PRIMER ( i i i ) HYPOTHETICAL: NO ( i v ) ANTI-SENSE: NO ( x i ) SEQUENCE DESCRIPTION: SEQ ID NO:5:

TTAAGCATTG CTCCAAGA                                                                                    18

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)
        ( A ) DESCRIPTION: 5 END PRIMER ( i i i ) HYPOTHETICAL: NO ( i v ) ANTI-SENSE: NO ( x i ) SEQUENCE DESCRIPTION: SEQ ID NO:6:

TATGACTCTG AATTCCTATA AGG                                                                              24

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)
        ( A ) DESCRIPTION: 5 END PRIMER ( i i i ) HYPOTHETICAL: NO ( i v ) ANTI-SENSE: NO ( x i ) SEQUENCE DESCRIPTION: SEQ ID NO:7:

CTACCTTAAG AATTCCTCCA AGAA                                                                             24

We claim:

1. A DNA probe for the detection of the presence of Candida strains in a biological sample, which consists of the following nucleic acid sequence:

CAACCTATAA GGGAGGCAAA AGTAGGGACG

CCATGGTTTC CAGAAATGGG

CCGCGGTGTT TTTGACCTGC TAGTCGATCT

GGCCAGACGT ATCTGTGGGT 100

GGCCAGCGGC GACATAACCT GGTACGGGGA

AGGCCTCGAA GCAGTGTTCA 150

CCTTGGGAGT GCGCAAGCAC AAAGAGGTGA

-continued

```
                    GTGGTGTATG GGGTTAATCC 200
CGTGGCGAGC CGTCAGGGCG CGAGTTCTGG
                    CAGTGGCCGT CGTAGAGCAC 250
GGAAAGGTAT GGGCTGGCTC TCTGAGTCGG
                    CTTAAGGTAC GTGCCGTCCC 300
ACAGCATGAA AAGTGTGCGG TGCAGAATAG
                    TTCCCACAGA ACGAAGCTGC 350
GCCGGAGAAA GCGATTTCTT GGAGCAATG
                                          379
                                    SEQ ID NO: 1,
``` or DNA molecules having homology thereto to specifically hybridize to the 25S rRNA gene of Candida detected with said probe.

2. A method for the detection of a trace amount of Candida in a biological sample, which comprises the steps of:
   a) isolating DNA from said biological sample;
   b) amplifying said isolated DNA of step a) with paired oligonucleotides:

5'primer: AAC TTA GAA CTG GTA CGG 3' (SEQ ID NO: 2)
   3'primer: AGT AGA TAG GGA CAG TGG 3' (SEQ ID NO: 3)
   or
   5'primer: GAC TCT CAA CCT ATA AGG 3' (SEQ ID NO: 4)
   3'primer: TTA AGC ATT GCT CCA AGA 3' (SEQ ID NO: 5)

c) isolating amplified DNA of step b) and determining the presence or absence of Candida in said biological sample by direct examination of the amplified products on stained gel or by nucleic acid hybridization.

3. A pair of DNA primers for use in the amplification of DNA from Candida, said DNA from Candida consisting of:
   a) SEQ ID NO:1; or
   b) DNA molecules having homology thereto to specifically hybridize to the 25S rRNA gene of Candida whose DNA is amplified by said primers.

* * * * *